United States Patent
Pilo et al.

(10) Patent No.: US 6,589,258 B2
(45) Date of Patent: Jul. 8, 2003

(54) DISPOSABLE SURGICAL SAFETY SCALPEL

(76) Inventors: Giuseppe Pilo, Via Muroni 22, 07100 Sassari (IT); Antonio Giovanni Flumene, Via Garavetti 6, 07100 Sassari (IT)

(*) Notice: Subject to any disclaimer, the term of this patent is extended or adjusted under 35 U.S.C. 154(b) by 0 days.

(21) Appl. No.: 10/030,050

(22) PCT Filed: May 9, 2001

(86) PCT No.: PCT/EP01/05289
§ 371 (c)(1),
(2), (4) Date: Jan. 8, 2002

(87) PCT Pub. No.: WO01/85039
PCT Pub. Date: Nov. 15, 2001

(65) Prior Publication Data
US 2003/0105479 A1 Jun. 5, 2003

(30) Foreign Application Priority Data
May 10, 2000 (IT) .......................... SS2000A03

(51) Int. Cl.[7] .............................. A61B 17/32
(52) U.S. Cl. ............................ 606/167
(58) Field of Search ............... 606/166, 167, 606/170, 172, 181, 182; 30/162, 335, 336

(56) References Cited
U.S. PATENT DOCUMENTS

| | | | | |
|---|---|---|---|---|
| 3,879,847 A | * | 4/1975 | Roll ............................ 30/162 |
| 4,277,888 A | * | 7/1981 | Szabo ......................... 30/162 |
| 4,757,612 A | * | 7/1988 | Peyrot ......................... 30/151 |
| 5,071,426 A | * | 12/1991 | Dolgin et al. ............... 606/167 |
| 5,139,507 A | * | 8/1992 | Dolgin et al. ............... 606/167 |
| 5,299,357 A | * | 4/1994 | Wonderley et al. .......... 30/339 |
| 6,022,364 A | | 2/2000 | Flumene et al. |

FOREIGN PATENT DOCUMENTS

WO   WO 93/25152   * 12/1993   ........... A61B/17/32

* cited by examiner

Primary Examiner—Michael J. Milano
Assistant Examiner—D. Jacob Davis
(74) Attorney, Agent, or Firm—Young & Thompson

(57) ABSTRACT

A disposable surgical safety scalpel comprising a blade, fixed at one end to an elongated support or slider, sliding longitudinally inside a protective shell, to bring the blade from a retracted inoperative position, in which it is housed inside the shell, to an exposed operative position, through the action of an operator who acts on a push-button mounted on the support; a safety shield longitudinally slidably mounted on the shell, the shield moving from an advanced position, in which it covers the push-button, when the push-button is in its retracted inoperative position, for preventing the push-button from involuntary driving, to a retracted position, in which the shield does not cover the push-button; and elastic return elements to bring the blade back into the retracted inoperative position, the elastic elements acting between the support and the safety shield, such that the shield can automatically and involuntary cover the push-button, when the support is brought in its retracted inoperative position by the elastic elements.

11 Claims, 5 Drawing Sheets

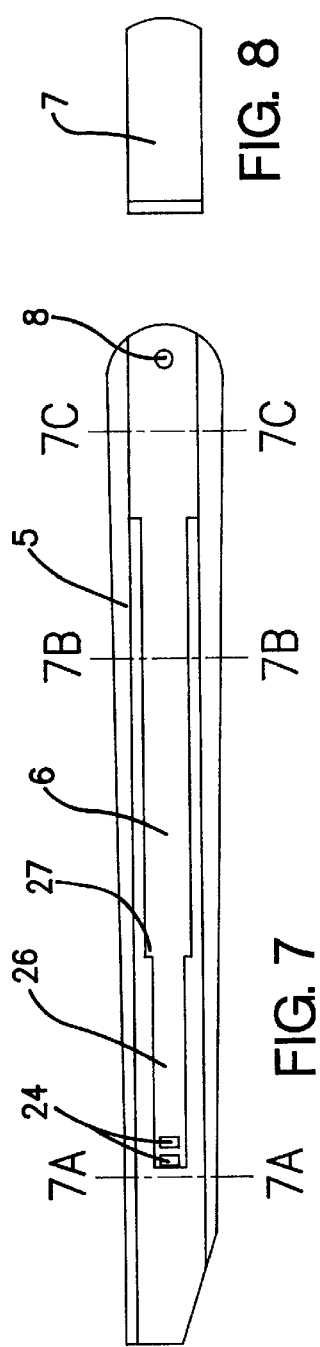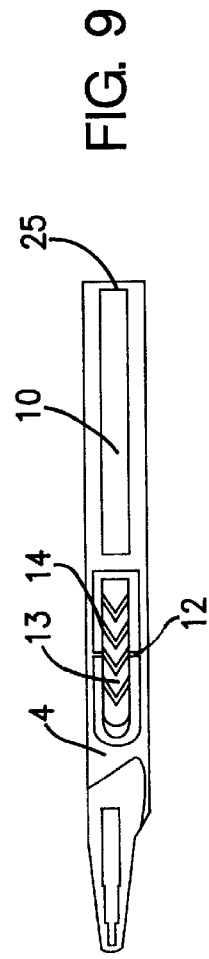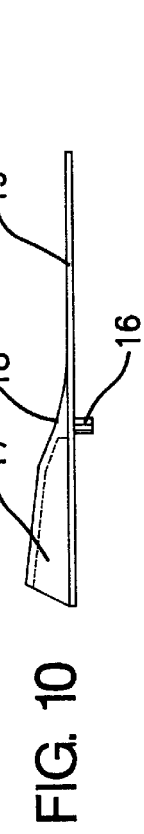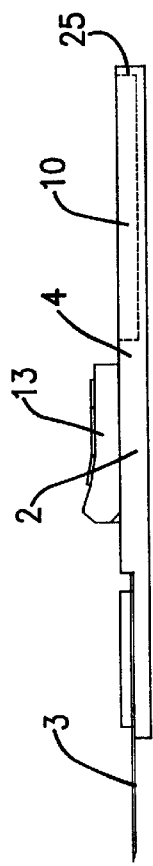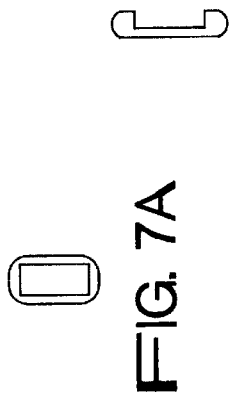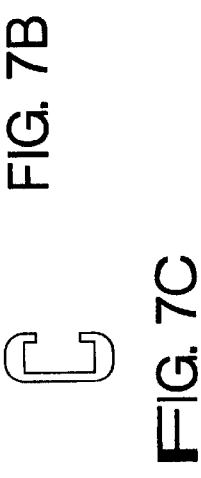

DISPOSABLE SURGICAL SAFETY SCALPEL

The present invention relates to a disposable surgical safety scalpel for medical use, having a retractable blade.

A scalpel is a highly professional surgical instrument which has been perfected over the years to such an extent that it cannot be compared to a jack knife or a cutter.

In describing the prior art, reference can be made only from an historical viewpoint to some patents relating to knives described in the more or less recent past, whose characteristic was to have a blade that is positioned after use in a protective container.

This is the case, for example, of the following patents:
- GB- 5487 (LAKE), which as far back as 1884 described a knife with an extractable blade;
- U.S. Pat. No. 4,028,758 (O'CONNOR), which describes a combination of a utility knife and a staple remover;
- U.K.-1511889 (STEABBEN), which describes a pocket cutter with a blade that retracts but not automatically;
- U.S. Pat. No. 4,769,912 (DAVIS), which describes a knife with an acceleration sensor;
- U.S. Pat. No. 4,858,320 (LEMAIRE), which describes a pocket knife with retractable blade;
- DE-3735294 (TEIHS), U.S. Pat. No. 4,835,865 (KNOOP) and lastly BE.1.002.554 (VAN HOOYDONCK), which describe an industrial cutter with retractable blade.

As it is well known, the surgical scalpels existing on the market are of the disposable or reusable type, with a fixed or interchangeable blade, and do not normally have any protection, except for a blade protecting cap in the case of disposable scalpels, which cap is slipped off before use and could be replaced after use.

In fact the cap should never be replaced because this maneuver can cause unwelcome cuts, with the risk of transmission of diseases, including serious ones like AIDS and viral hepatitis.

The use of a barrier system, such as gloves with a steel mesh, which protect from cuts but not from stab wounds, is not well accepted because of the increased thickness and stiffness of the gloves, which leads to a loss of sensitivity.

The use of a different system, called "Magnetic Drape", which consists of a sort of magnet cloth to be placed near the operating field and to which the surgical instruments adhere through the action of a magnet, avoids the stage of passing the instruments from hand to hand, thus eliminating some wounds, i.e. those that occur during exchange of instruments between operators.

This system is poorly received by surgeons because it is essential to look away from the operating field to grasp the instrument and also because it is of no use for non-metallic objects.

The majority of accidental scalpel stab wounds or cuts occurs not so much when the surgeon makes an incision in the patient's skin or tissue as when the scalpel is passed from hand to hand by the medical operators or during disposal.

A study published in the USA in April 1995 by Dr. Janine Jagger in "Advances in exposure prevention", Volume 1 No. 3 published by "INTERNATIONAL HEALTH CARE WORKER SAFETY RESEARCH AND RESOURCE CENTER" showed that 34% of scalpel wounds occur during use of the instrument, whilst the remaining 39% and 27%, respectively, take place when the scalpel is passed from hand to hand by operators and during removal replacement-disposal of the blade.

From these data it emerges that, overall, scalpels with an exposed blade or an interchangeable blade are responsible for 66% of cut wounds that occur among medical operators before, during and after use of the instrument.

It is for this reason that all scalpels with an exposed blade, such as those currently on the market, must be considered dangerous, as well as those with an interchangeable blade, such as those forming the object of the following patents:
- PCT-WO 90/11725 (DOLGIN), which describes a metal scalpel with a mobile guard, with no automatic return and requiring replacement of the blade;
- U.S. Pat. No. 5,250,063 (ABIDIN), which describes a metal scalpel with a mobile guard and an interchangeable blade;
- PCT-WO 94/13216 (WERNER), which describes a metal scalpel with a voluntarily and automatically retracting blade that is extremely dangerous in that, pressure exerted on the rear part causes an accidental forward movement of the blade, is difficult to construct and also has an interchangeable blade;
- PCT-WO 95/15723 (GHARIBIAN), which describes a scalpel with a mobile guard and interchangeable blade without any locking system between the cap and the blade holder, making it difficult to use and dangerous;
- PCT-WO 93/24064 (NEWMAN P. H.) and U.S. Pat. No. 5,403,337 (PLATTS) which describe a disposable scalpel with a blade that can be changed during the surgical procedure, without foreseeing any protection for used blades.

Changing of the blade is in fact the weak point of any instrument, even those considered safe, because handling necessarily leads to an increased risk of accidental wounds.

In the analysis of the prior art it can be seen that as time went on, inventors refined the idea of a safe scalpel to meet the need for protection required by surgeons.

Starting from mobile blade protection system without automatic return, such as, for example, those described in patents:
- U.S. Pat. No. 3,905,101 (SHEPHERD), U.S. Pat. No. 3,906,626 (RIULI), U.S. Pat. No. 4,414,974 (DOTSON), EP-0 251 485 (GORDY), U.S. Pat. No. 4,735,202 (WILLIAMS), EP-0 612 506 (NEWMAN C. D.), whose main defects lie in the need to use both hands to set up or to protect the instrument and the necessity to remember to cover the blade each time it is passed from hand to hand, systems have been designed with a mobile blade guard that can be moved with only one hand, but still without automatic return of the cap, such as those described in patents:
- PCT-WO 90/11725 (DOLGIN), U.S. Pat. No. 5,250,063 (ABIDIN), U.S. Pat. No. 5,417,704 (WONDERLEY), PCT-WO 95/15723 (GHARIBIAN), in which advancement and retraction of the protective cap is carried out with one hand and must be intentional on the part of the operator.

Again with regard to mobile guard, the following patents must be considered separately:
- U.S. Pat. No. 5,330,492 (HAUGEN), which describes a scalpel with a guard that can be moved by means of a push-button, which when pressed causes the protective cap to retract, uncovering the blade, and when released unintentionally causes the opposite effect; this instrument must be grasped in a an unnatural way, does not offer guarantees of safety because the push-button protrudes excessively and in addition, because of its excessive height, does not allow a correct cutting angle on the skin surface;
- U.S. Pat. No. 5,330,494 (VAN DER WESTHUIZEN), which describes a guard that can move transversely to the blade, constituting a danger not only for the operators, because pressure exerted-casually on the lower edge of the cap causes uncovering of the blade with a high risk of wounds, but also for patients, since the cutting force cannot be regulated.

More recently different systems have been proposed, such as, for example, that in U.S. Pat. No. 5,116,351 (FRASSETTI), which describes a mobile blade mechanism, with automatic return of the blade to the protected position and with the possibility of voluntary locking, but it is basically awkward, because it obliges the operator to work in an unnatural position, that is with the finger exerting a certain pressure on the upper edge of the blade and with the blade partly covered by the protection system;

and that of U.S. Pat. No. 5,207,696 (MATWIJCOW), which describes a scalpel with a retractable blade and mobile guard, but which seems too bulky and therefore awkward and has no automatic involuntary return of the blade to the covered position.

A further development in the design of these instruments has come about with a concept that foresees the possibility of extracting the blade from the handle. This is probably the idea that holds most advantages, because it offers interesting solutions to the problems described up to now, although each of the ideas proposed gives rise to some considerations as regards their practical operation.

A first proposal for a retractable blade is presented in:

EP-0 217 638 (DESATNICK), which describes an instrument for closed cavity surgery, with a small retractable blade, without automatic return, not disposable, therefore dangerous during blade changes, and not suitable for skin incisions;

PCT-WO 93/24064 (NEWMAN P. H.), which describes a scalpel with locking of the exposed blade, which is very difficult to set up, with voluntary return, with the risk of the blade holder with the blade coming out accidentally from the rear part of the cover, without any protection against an accidental forward movement of the blade and with the possibility of replacing the blades during a surgical procedure, an operation which seems dangerous because the exposed blade is handled;

U.S. Pat. No. 5,330,493 (HAINING) which describes a disposable scalpel with a retractable blade, without automatic return of the blade to the resting position, with a button for forward movement of the blade that is situated on its upper edge and is therefore awkward to slide, and with a permanent end-of-use lock, which seems superfluous and could sometimes be applied accidentally, thus making it impossible to use the instrument;

PCT-WO-94/13216 (WERNER), which describes a metal scalpel with voluntary automatic retraction of the blade that is extremely dangerous because a pressure exerted on its rear part causes an accidental unintentional forward movement of the blade. Said metal scalpel is difficult to construct and furthermore has an interchangeable blade;

U.S. Pat. No. 5,344,424 (ROBERTS) which presents a disposable scalpel with voluntary retraction, with three locking positions, i.e. an operative or set up position, an inoperative position and a safety position, where the only innovation appears to be the internal safety device, but which is difficult to handle and dangerous because the blade advance system protrudes too far;

U.S. Pat. No. 5,531,754 (SHACKELFORD), which presents a scalpel with voluntary retraction, but dangerous because the blade advance system protrudes too high;

EP-0 622 047 (DERBYSHIRE), which describes an original blade advance system in which pressure is exerted on a flexible container (balloon), with automatic spring-operated return, with the defect that seeing the blade retract each time, pressure is exerted on skin or tissues because of the intrinsic elasticity of the balloon itself, and the blade can accidentally move forward through unintentional pressure exerted by other instruments or hands;

U.S. Pat. No. 5,403,337 (PLATTS), which describes a scalpel wholly similar to the one described in PCT-WO 93/24064 (EWMAN P. H.), criticizing it as awkward and dangerous and adding its own small modification to eliminate these defects, but making it more difficult to set up with only one hand (the rear part of the handle has been widened to allow for positioning of two stops) and still foreseeing blade changes during the surgical procedure, which continues to represent a hazard;

U.S. Pat. No. 5,431,672 (COTE), which presents a scalpel with automatic, voluntary return of the blade with an additional internal lock, which could be accidentally applied during surgical procedures, forcing the medical staff to use a new scalpel;

PCT-WO-95/24855 (DILLON), which shows a scalpel with automatic, voluntary blade return, with an unsafe stopping system for the exposed blade and with locking devices not better identified to avoid re-use;

PCT-WO 93/25152 (FLUMENE et al.), which presents a disposable scalpel with rear lock to prevent any accidental forward movement of the blade, with easy blade exposure, without any locking in the operative or set up position of the blade, so as to have automatic, involuntary return and locking in the resting position; moreover, a particular characteristic is the possibility of graduating extraction of the blade according to the type of incision, always acting on the instrument in a comfortable, ergonomic position; the only drawback to be noted is that since it does not have a forward lock, use of this instrument is rather awkward in some operating conditions, so the presence of a stop device for the blade in operative position could be desirable in some circumstances;

U.S. Pat. No. 6,022,364 (FLUMENE et al.), which describes a disposable scalpel with the same features of PTC-WO 93/25152, but with a blade's voluntary lock in position of use, which the operator can operate or not, depending on how he prefers to work. The scalpel has a further lock-safety-cover system, which operates at the end of a retraction stroke of the blade, thus avoiding an accidental emerging of the same.

The aim of this invention is, therefore, to solve some of the drawbacks posed by the prior art.

In particular, an aim of the invention is to provide a scalpel that is safe when passed among the operators, protected during transport and disposal of used materials, and to offer different possibilities of use, so that it is accepted by virtually all users, irrespective of their preferences for handling of the instrument.

Another aim of the invention is to provide safety locks for the blade that can easily be removed by moving one finger of the hand holding the scalpel, which is the same finger used to advance the blade.

Yet another aim of the invention is to provide a safety scalpel of the above type that is easy to make, automatically assemblable and economical.

A surgical safety scalpel in accordance with the invention is characterized by the characteristics listed in appended independent claim 1.

Essentially, the scalpel according to the invention is provided with a voluntary locking means for intentionally locking the blade in position for use, which the operator can operate or not, depending on how he prefers to work.

If this locking means is operated, it must be disabled after use to allow return of the blade.

However, this maneuver is extremely simple and does not require particular care on the part of the user.

An essential feature of the present invention lies in the presence of an automatic safety-cover system of the push-button of the blade, which automatically operates at the end of a retraction stroke of the blade, thus avoiding an unintentional driving of the push-button and therefore an accidental emerging of the blade.

An advantage of the present invention lies in the fact that the maneuvers made on the scalpel (retracting the push-button cover—advancing the blade—inserting and releasing the front lock of the blade when required) are effected by means of a single finger of a same hand, keeping the scalpel in its correct use position and leaving the other hand free to make another action.

Further characteristics of the invention will be made clearer by the following detailed description, referring to purely exemplary and therefore non-limiting embodiments thereof, illustrated in the appended drawings, in which:

FIG, 1 is a top plan view of a scalpel according to the invention, with the blade retracted inside the shell, in an inoperative position;

FIG. 7 is a top plan view of the safety handle of the scalpel;

FIGS. 7A, 7B, 7C are cross-sections taken along the planes A—A, B—B and C—C, respectively, in FIG. 7;

FIG. 8 is a plan view of the rear plug of the safety handle;

FIG. 9 is a top plan view of the sliding blade support, to be assembled inside the safety handle;

FIG. 10 is a lateral view of safety cover member of the blade push-button;

FIG. 11 is a lateral view of the sliding blade support, that must be assembled and fitted inside the safety handle;

Figure 1:
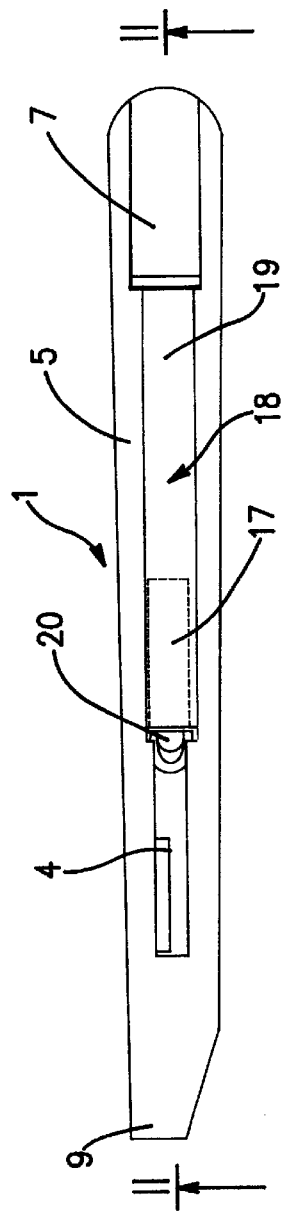

With reference to the appended drawings, and for now to FIGS. 1–6 in particular, a safety scalpel, according to the invention, has been designed as a whole with reference numeral 1.

It comprises a scalpel proper 2, consisting of a blade 3 and an elongated support 4, and a shell or outer case 5, acting as a handle, made in two members: the shell proper 5 and a rear closure or plug 7, joined together by mortising.

Figure 3:
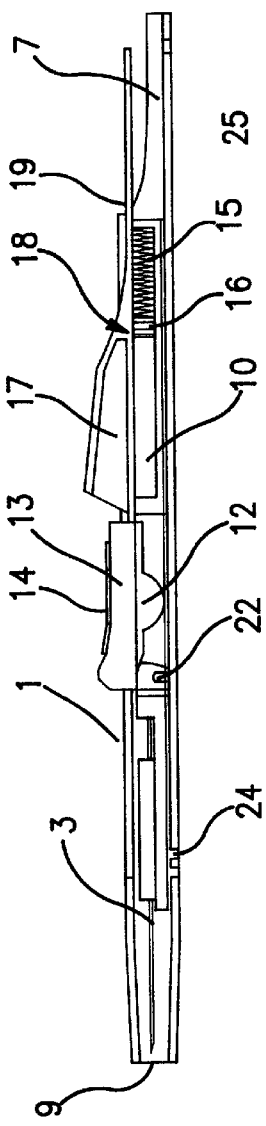
FIG. 3 is a median sectional view, taken along the line II—II in FIG. 1, showing the push-button safety cover member in a retracted position.
Figure 4:
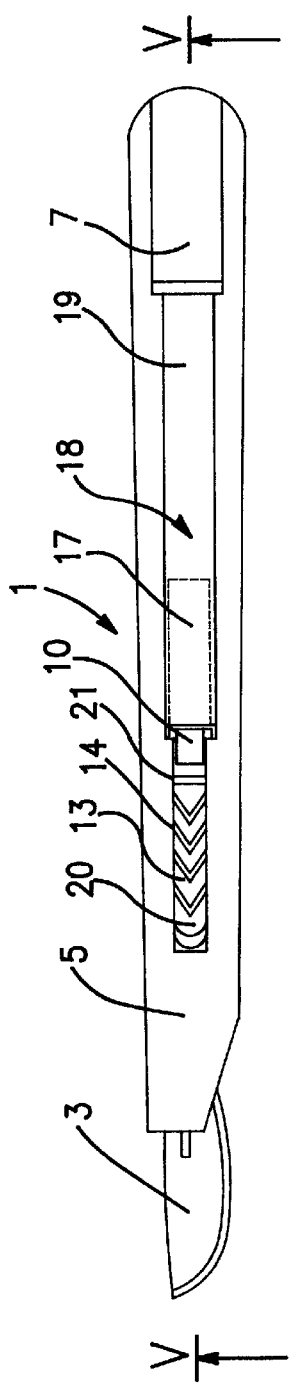
FIG. 4 is a top plan view of the scalpel in FIG. 1, with the blade extracted, in the operating position.
Figure 5:
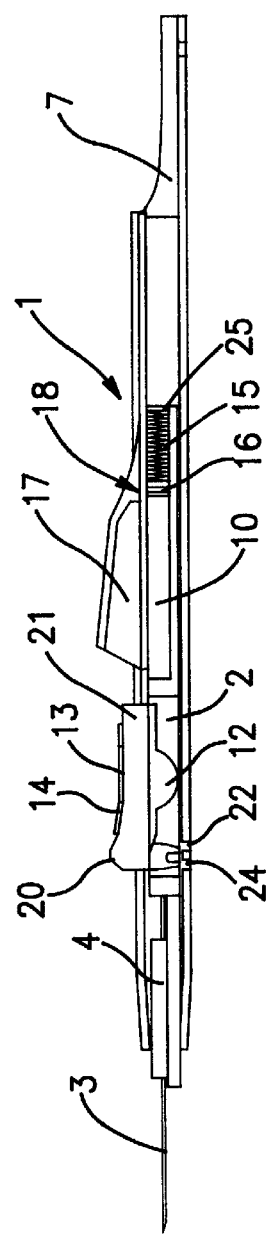
FIG. 5 is a median sectional view taken along the line V—V in FIG. 4, showing the blade extracted, in the operating position, not locked with the voluntary lock.
Figure 6:
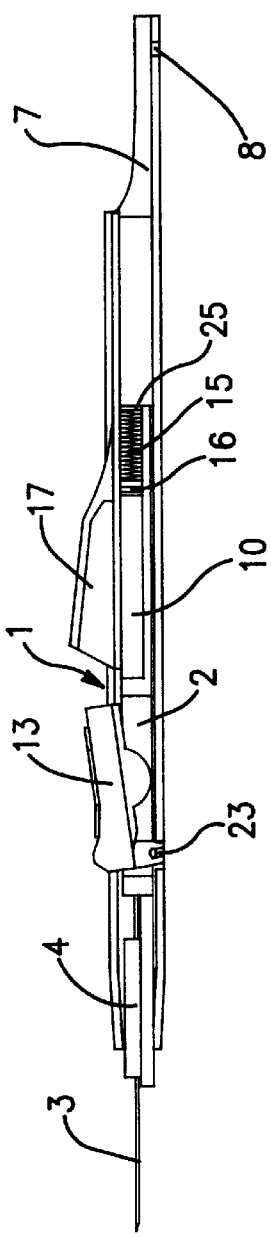
FIG. 6 is a median sectional view taken along the line V—V in FIG. 4, showing the blade extracted, in the operating position, locked with the voluntary lock.
Figure 12:
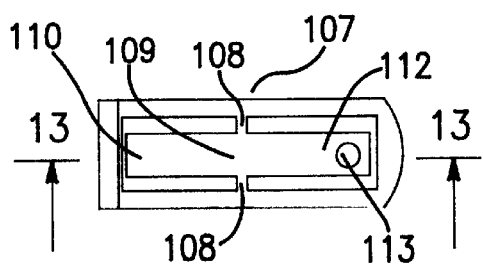
FIG. 12 is a top plan view of a second embodiment of the rear plug.
Figure 13:
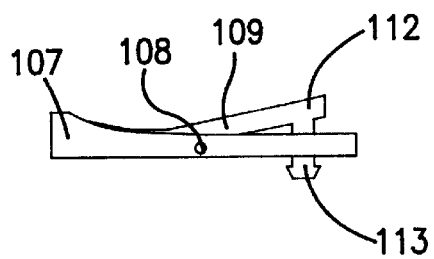
FIG. 13 is a lateral view of the second embodiment of the rear plug in an unlocked position.
Figure 12A:
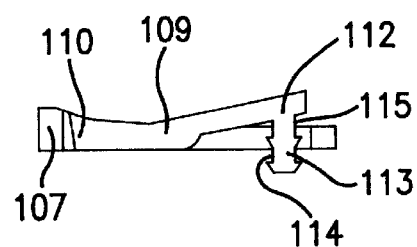
FIG. 12A is a median sectional view, taken along the line A—A in FIG. 12, showing the rear plug in an unlocked position.
Figure 14:
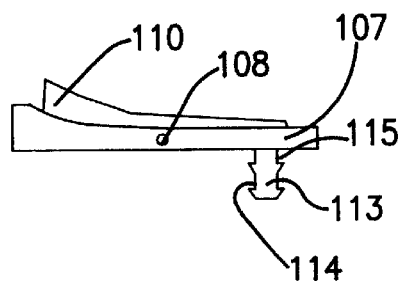
FIG. 14 is a lateral view of the second embodiment of the rear plug in a locked position.
Figure 12B:
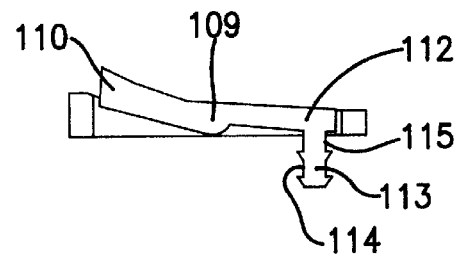
FIG. 12B is a median sectional view, taken along the line A—A in FIG. 12, showing the rear plug in a locked position.
Figure 15:
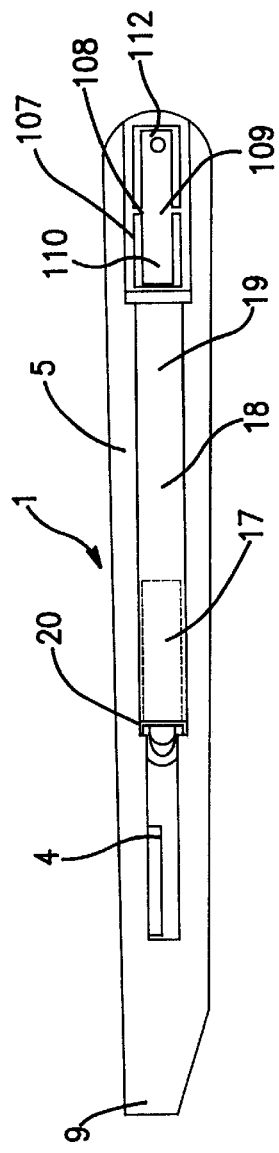
FIG. 15 is a top plan view of the scalpel with the second embodiment of the rear plug.

The scalpel 2 is housed inside the shell 5, which has two ends, an anterior open end 9 and the opposite end closed by the plug 7, and has the possibility of sliding longitudinally, in such a way that the blade 3 can be brought from a resting or inoperative position in which it is housed completely inside the shell 5 (FIGS. 1, 2 and 3), to an operative position or position for use, in which it projects from the open end 9 of the shell 5 (FIGS. 4, 5 and 6).

The elongated support 4 of the blade 3 acts as a slider and is guided between the side walls of the shell 5. Referring to FIG. 7 on one of these side walls, a longitudinal aperture or window 6 is provided, with a substantially rectangular shape, with a narrowing 26 at the front, on the part wherein the blade 3 is positioned. The front narrowing 26 creates an abutment surface 27 in the window 6.

A push-button or pivoted button 13 of the support 4 is provided in the window 6, protruding only slightly from the window 6, the operator being able to operate said button with one finger to cause the support-slider 4 to slide. To make the button 13 easier to grip, normally with the thumb, herring-bone ribs 14 are provided on it.

The support 4 is held in its retracted position when it is housed inside the shell 5 by an elastic means, in particular by a compression spring 15 operating between a small pin 16 projecting downward from a safety cover 18 (hereinafter called shield) of push-button 13 and the rear wall 25 of a cavity 10 for housing the spring 15, located in the rear part of the support 4 of the scalpel proper 2.

The oscillating button 13 pivots on a pin 12, disposed transversely to the support 4.

The push-button 13 is so shaped that its rear part 21 (with reference to the appended figures), has a lower height than the height of the front part 20, to easier the grip of the user.

A circular open housing 22, provided below the push-button 13, in the front part thereof, engages a transversal pin 23 provided in an opening 24 of the handle 5, when the user voluntarily operates the button 13, thus providing a voluntary lock for the blade in condition of use.

FIGS. 1–6 and 10 also show the safety shield 18 covering the push-button 13, that is the shield 18 is able to prevent the push-button 13 from accidentally driving and to prevent therefore the blade from emerging, when the scalpel is passed from hand to hand. The shield 18 slides longitudinally into the side walls of the window 6 between the support 4 and the shell 5.

The safety shield 18 comprises a safety cover 17, C-shaped in cross section, on the front part thereof, covering the push-button 13 (see FIGS. 1 and 2), preventing any pressure on the push-button itself; and a lug 19 on the rear part thereof, covering the spring 15 housed in the cavity 10.

The pin 16, projecting from the lower part of the shield 18, pushes the spring 15 to the rear wall 25 of the cavity 10. Therefore, the shield 18 can slide from an advanced position, wherein its front end is in abutment against the abutment surface 27 of the narrowing 26 of the window 6 of the shell 5 to a retracted position, wherein the spring 15 is compressed between the pin 16 and the wall 25 of the support 4. When the shield is in the advanced position, it covers the push-button 13; when it is in retracted position, the push-button 13 is uncovered.

FIGS. 12–17 show a second embodiment of the rear plug 7, which is designed as a whole with reference numeral 107.

The rear plug 107 comprises an oscillating push-button 109, that pivots on two aligned pins 108, fitted transversely to a frame of the rear plug 107. The oscillating push-button 109 comprises a rear part 112 with a pin 113 protruding downward therefrom. The pin 113 comprises two radially protruding collars, delimiting a first and a second annular notch 114, 115, respectively.

A through hole 8 is provided in the rear part of the shell 5, better shown in FIG. 8. When the rear plug 107 is assembled in the rear part of the shell 5, the pin 113 engages the hole 8, and precisely the first notch 114 of the pin 113 is engaged into the hole 8. In this condition, (FIG. 16), the front end 110 of the oscillating push-button 109 is at the same level of the frame of the rear plug 107 and the scalpel is in operative condition.

Figure 16:
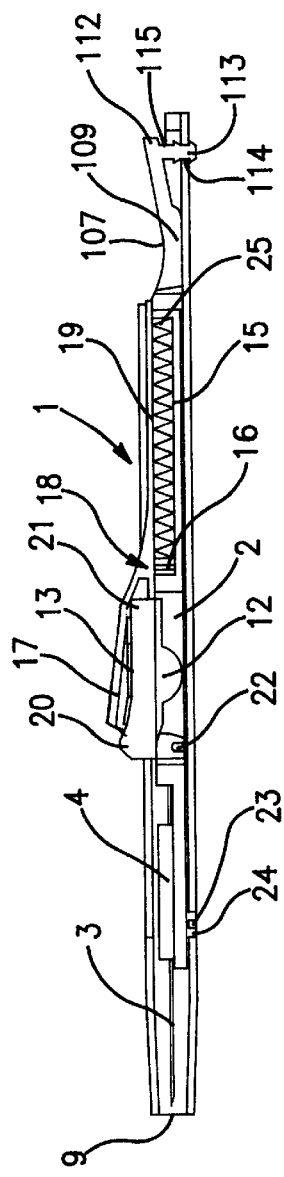
FIG. 16 is a median sectional view, as FIG. 2, showing the scalpel with the second embodiment of the rear plug in an unlocked position.
Figure 17:
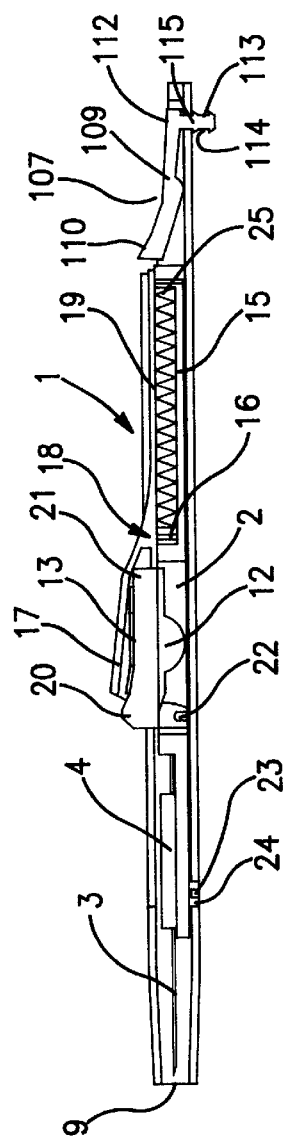
FIG. 17 is a median sectional view, as FIG. 2, showing the scalpel with the second embodiment of the rear plug in a locked position.

The working position of the button 109 (as shown in FIG. 16) allows the sliding movement of the shield 18, since the rear end of the shield 18 does not interfere with oscillating push-button 109.

At the end of the surgical operation, before the disposal of the scalpel, the user has merely to press the rear part 112 of the oscillating push-button 119 of the rear plug 107; thus the pin 113, housed in the hole 8 with the first notch 114, penetrates in the hole 8 more deeply up to the second notch 115. After this movement, the front part 110 of the push-button 109 protrudes upwardly from the frame of the rear plug 107 and it is opposed to the rear part 19 of the shield 18 and therefore the scalpel cannot be used again.

The scalpel according to the invention works as follows.

Figure 2:
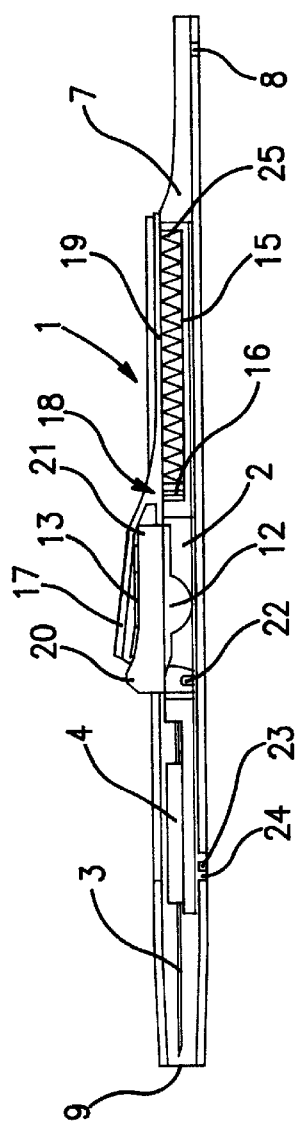
FIG. 2 is a median sectional view, taken along the line 11—11 in FIG. 1.

When the scalpel is not in use, the spring 15 holds the scalpel 2 in a retracted position inside the shell 5, as shown in FIGS. 1 and 2, by a combined action of the spring 15, the scalpel 2 and the shield 18. One of the two contact points of the spring 15 is the pin 16 of the shield 18, and the other contact point is the rear wall 25 of the cavity 10 of the scalpel proper 2.

The scalpel proper 2 is housed inside the shell 5, longitudinally sliding therein. The rear cover 7 or 107 prevents the scalpel proper 2 from exiting from the rear end of the shell 5.

Only the scalpel blade 3 can emerge from the front opening 9 of the shell 5. The scalpel proper 2 is prevented from extraction from the front end of the shell 5 because the front end of the push-button 13 abuts against the front end of the restriction 26 of the window 6 of the shell 5.

Starting from the position shown in FIGS. 1 and 2, in order to use the scalpel, it is first necessary to move the safety shield 18 backwards, with the thumb of one hand, as shown in FIG. 3. It is therefore sufficient to exert a light pressure on the pivoted push-button 13, with the same thumb, and push the button 13 forwards, in the direction of the open end 9 of the shell 5, so as to cause the blade 3 to emerge, as shown in FIGS. 4 and 5.

In this condition, the scalpel is ready for use, without the blade being locked in this position, said locking takes place only through a voluntary action on the part of the surgeon, as it will be seen with reference to FIG. 6.

Remaining within the context of FIGS. 4 and 5, after use of the instrument, simply releasing the push-button 13 causes the blade to return automatically inside the shell 5, through the action of the spring 15, with consequent automatic and involuntary covering of the push-button by the shield 18.

The use of the scalpel shown in FIGS. 4 and 5, without locking of the blade, is suitable for that group of users that prefers automatic and involuntary return of the blade 3 after use, without any maneuver having to be carried out.

An alternative use of the scalpel according to the invention is shown in FIG. 6, in which locking of the blade 3 has taken place, through a voluntary action by the user, by means of engagement of the housing 22 of the button 13 with the pin 23 provided in the shell 5.

After use of the scalpel, pressure must be exerted on the rear part 21 of the pivoted push-button 13, to cause the disengagement of the housing 22 of the push-button from the pin 23 of the shell 5 and therefore the unlocking of the blade and its automatic and voluntary return inside the shell 5.

The shell 5, the support 4 and the pivoted push-button 13 are advantageously made of plastic, whilst the spring 15 can be of plastic, metal, rubber or with an air or gas system or the like.

It is also obvious that the blade 3 can have any shape, depending on its use, without the characteristics of the scalpel according to the invention undergoing any changes.

To aid voluntary locking of the blade in the position for use (FIG. 6), the horizontally pivoting push-button 13 has the raised part 20 at the front, which facilitates the lowering action to cause engagement of its housing 22 with the pin 23.

According to the embodiment shown in FIGS. 12–17, at the end of the operation it is possible to put the scalpel in a safe condition, pressing the rear part 112 of the button 109, housed in the rear plug 107. This position definitively locks the shield 18, making the scalpel not reusable and no longer dangerous.

What is claimed is:

1. A disposable surgical safety scalpel comprising:
   a blade (3), fixed at one end to an elongated support or slider (4), sliding longitudinally inside a protective shell (5), to bring said blade (3) from a retracted inoperative position, in which it is housed inside the shell (5), to an exposed operative position, through the action of an operator who acts on a push-button (13) mounted on said support (4);
   a safety shield (18) longitudinally slidably mounted on said shell (5), said shield (18) moving from an advanced position, in which it covers said push-button (13), when said push-button is in its retracted inoperative position, for preventing the push-button from involuntary driving, to a retracted position, in which said shield does not cover said push-button; and
   elastic return means (15) to bring the blade (3) back into the retracted inoperative position,
   characterized in that
   said elastic return means (15) act between said support (4) of the blade (3) and said safety shield (18), so that said shield (18) can automatically and involuntary cover the push-button (13), when said support (4) is brought in its retracted inoperative position by said elastic means.

2. The scalpel according to claim 1, characterized in that a cavity (10) is provided in the rear part of said support (4), said cavity (10) being able to house said elastic return means (15), which act between a pin (16) protruding downwardly from said shield (18) and a rear end wall (25) of said cavity (10) of said support (4).

3. The scalpel according to claim 1, characterized in that said shield (18) comprises a front part (17) having a substantial C shape in cross-section, able to cover said push-button (13) and a substantial flat rear part (19) located onto said shell (5).

4. The scalpel according to claim 1, characterized in that said support (4) is housed into the shell (5) between the side walls of the shell and is covered by the shield (18), so that said shield (18) and said support (4) can slide on parallel surfaces, and said elastic means (15) can guarantee both the return of said support (4) in the shell (5) and the positioning of said shield (18) in said advanced position covering the push-button (13).

5. The scalpel according to claim 1, characterized in that said shell (5) comprises a front stop member (27) to stop the forward stroke of side shield (18) and a rear stop member (7, 107) to stop the reverse stroke of said support (4) and/or said shield (18).

6. The scalpel according to claim 5, characterized in that said front stop member is an abutment surface (27) of a narrowing (26) of a window (6) of said shell (5) which allows sliding of said push-button (13) and said shield (18), and said rear stop member is a rear plug (7; 107) able to be fitted in the rear part of said shell (5).

7. The scalpel according to claim 6, characterized in that said rear plug (107) comprises locking means (109) to lock/unlock said shield (18).

8. The scalpel according to claim 7, characterized in that said locking means is an oscillating push-button (109) having a front part (116) able to abut against the rear end of the shield (18) to lock it and a rear part having a pin (113) protruding downwardly therefrom to engage into a hole (8) provided in said shell (5).

9. The scalpel according to claim 8, characterized in that said pin (113) has two collars delimiting a first notch (114) and a second notch (115) which define with said hole (8) a first engaging position, in which the push-button (109) does not lock the shield (18) and a second engaging position, in which the push-button (109) locks the shield (18).

10. The scalpel according to claim 1, characterized in that said push-button (13) is pivotly mounted on said support (4) and provides engaging means (22) engageable with respective engaging means (23) provided in said shell (5) by means of voluntary pression on said push-button (13) by the user, when the blade is in said exposed position.

11. The scalpel according to claim 2, characterized in that said shield (18) comprises a front part (17) having a substantial C shape in cross-section, able to cover said push-button (13) and a substantial flat rear part (19) located onto said shell (5).

* * * * *